United States Patent [19]
Cazin et al.

[11] Patent Number: 6,102,912
[45] Date of Patent: Aug. 15, 2000

[54] VERTEBRAL ROD OF CONSTANT SECTION FOR SPINAL OSTEOSYNTHESIS INSTRUMENTATIONS

[75] Inventors: Muriel Cazin, Bussy St-Georges; Jean-Charles Moreau, Gouvieux, both of France

[73] Assignee: Sofamor S.N.C., France

[21] Appl. No.: 09/085,920

[22] Filed: May 28, 1998

[30] Foreign Application Priority Data

May 29, 1997 [FR] France .................................. 97 06620

[51] Int. Cl.[7] .................................................. A61B 17/56
[52] U.S. Cl. ............................................................ 606/61
[58] Field of Search ............................. 606/61, 60, 72, 606/73; 623/17

[56] References Cited

U.S. PATENT DOCUMENTS

| | | | |
|---|---|---|---|
| 4,361,141 | 11/1982 | Tanner | 128/69 |
| 4,658,809 | 4/1987 | Ulrich et al. | 606/61 |
| 4,697,582 | 10/1987 | William | 128/69 |
| 4,719,905 | 1/1988 | Steffee | 128/69 |
| 4,771,767 | 9/1988 | Steffee | 128/69 |
| 4,815,453 | 3/1989 | Cotrel | 128/69 |
| 4,854,304 | 8/1989 | Zielke | 128/69 |
| 5,154,718 | 10/1992 | Cozad et al. | 606/61 |
| 5,217,461 | 6/1993 | Asher et al. | 606/61 |
| 5,281,223 | 1/1994 | Ray | 606/61 |
| 5,304,179 | 4/1994 | Wagner | 606/61 |
| 5,330,472 | 7/1994 | Metz-Stavenhagen | 606/61 |
| 5,334,203 | 8/1994 | Wagner | 606/61 |
| 5,336,223 | 8/1994 | Rogers | 606/61 |
| 5,395,370 | 3/1995 | Muller et al. | 606/61 |
| 5,403,314 | 4/1995 | Currier | 606/61 |
| 5,425,732 | 6/1995 | Ulrich | 606/61 |
| 5,486,174 | 1/1996 | Fournet-Fayard et al. | 606/61 |
| 5,562,660 | 10/1996 | Grob | 606/61 |
| 5,575,790 | 11/1996 | Chen et al. | 606/61 |
| 5,591,165 | 1/1997 | Jackson | 606/61 |
| 5,593,408 | 1/1997 | Gayet et al. | 606/61 |
| 5,630,816 | 5/1997 | Kambin | 606/61 |
| 5,649,925 | 7/1997 | Barbera Alacreu | 606/61 |
| 5,653,710 | 8/1997 | Harle | 606/61 |
| 5,658,286 | 8/1997 | Sava | 606/61 |

FOREIGN PATENT DOCUMENTS

| | | | |
|---|---|---|---|
| 2 726 995 | 5/1996 | France | A61B 17/60 |
| 3624067 A1 | 2/1987 | Germany . | |
| 2 208 476 | 4/1989 | United Kingdom | A61B 17/56 |

*Primary Examiner*—Michael Buiz
*Assistant Examiner*—Tan-Uyen T. Ho
*Attorney, Agent, or Firm*—Woodard, Emhardt, Naughton Moriarity & McNett

[57] ABSTRACT

A vertebral rod for fixation of a spine, the rod defining an outer cross section and including a detachable end portion also defining the same outer cross section. In one embodiment, the detachable end portion is connected to the remainder of the rod by a region of reduced strength. The region of reduced strength forms a fracture initiator defining an area of reduced outer cross section so that the detachable end portion can be broken off. In another embodiment, the rod defines a threaded opening and a threaded spigot, each extending along the longitudinal axis of the rod. The spigot threadedly engages the opening to releasably connect the detachable end portion to the remainder of the rod. In either embodiment, the detachable end portion is configured to receive a driving tool for removing the detachable end portion from the remainder of the rod.

19 Claims, 6 Drawing Sheets

VERTEBRAL ROD OF CONSTANT SECTION FOR SPINAL OSTEOSYNTHESIS INSTRUMENTATIONS

BACKGROUND OF THE INVENTION

The present invention relates to a vertebral rod for a spinal osteosynthesis instrumentation, this rod having a constant diameter throughout its length and being adapted to receive bone anchorage implants. Complementarily, the invention also relates to a spinal osteosynthesis instrumentation comprising at least one of said rod and corresponding bone anchorage means fixed to the rod.

As is known, when an intervertebral disc is pinched, the adjacent vertebral bodies move toward each other and this causes a compression of the nerve roots and corresponding pain to the patient. It therefore becomes necessary to proceed to a surgical intervention to effect a correction, first by a distraction for separating the vertebral bodies and then by a compression for restoring the lumbar lordosis, i.e. the natural physiological curvature of the considered spinal segment.

In other cases, the vertebral column is deformed and asymmetric, which results in an abnormal curvature of the corresponding spinal segment. The surgical correction involves the use of implants fixed to the vertebrae and interconnected by a vertebral rod. In order to align the vertical column, a compression movement is necessary during which the implants slide along the rod and bring the vertebrae back to the desired orientation.

Subsequent to interventions of this type, the pain experienced by the subject is eliminated and the deformations are corrected. However, there remains a residual length of rod beyond the anchorage implants consituting a useless and even dangerous projecting part. Indeed, this end of the rod may alter the adjacent parts, in particular the articular elements located above and below, and damage the capsule of the upper articular elements.

This is the reason why some surgeons cut off this projecting end in situ. But such an operation requires large pliers for rods which may reach a diameter of 6 to 7 mm and cannot be effected without risk: indeed, the surgeon must exert a considerable force during which the pliers is liable to slip into the body of the patient and harm him, in particular after the inevitable jerk which occurs at the end of the cutting, and moreover the space taken up by the noses of the pliers is often excessive for the size of the spinal column.

Further, there is a definite risk of the ejection of the cut-off terminal member in the tissues, above all if the intervention occurs from the front. Indeed, the cut-off terminal member may drop into the peripheral muscles or behind the lungs or heart of the patient and become very difficult to remove. Lastly, the cut leaves an aggressive pointed end of the rod liable to harm the patient.

SUMMARY OF THE INVENTION

An object of the invention is therefore to provide a vertebral rod which is so arranged as to overcome this problem without risk for the patient, such a rod being of use for the correction of any vertebral deviation, in particular resulting from the degeneration of an intervertebral disc.

According to the invention, the vertebral rod, of constant section througout its length, is provided with a detachable terminal member of the same section as the rest of the rod.

With this arrangement, a bone anchorage implant is slidable in the course of this intervention on this terminal member, which can thereafter be separated from the rod at the end of the correction. It will be understood that the length of this terminal member may vary in accordance with the type of intervention.

As a non-limitative numerical example, the length of the detachable terminal member may be about 10, 15 or 20 mm.

According to one embodiment of the invention, the terminal member is connected to an end of the rod by a region of reduced strengh constituting a fracture initiator, whereby the terminal member can be broken off.

The separation of the terminal member from the rest of the rod at the end of the surgical intervention may be achieved by torsion or bending by means of a suitable tool.

According to another embodiment of the invention, the terminal member comprises an axial threaded spigot which can be screwed in a complementary tapped hole formed in one end of the rod.

The terminal member is then removed by unscrewing. The threaded spigot could be provided on the rod and screwed in a tapped hole in the terminal member. But this would be less advantageous than the preceding arrangement since, after the unscrewing of the terminal member, an undesirable projecting spigot would remain on the rod.

Any other connection between the terminal member and the rod may also be envisaged, for example a tapered fitting together.

Whatever mode of connection between the terminal member and the rest of the rod is used, the detachability of the terminal member after the rod and the corresponding instrumentation have been placed on the patient, eliminates the projecting end of the rod which becomes useless, whereas the initial length of the rod was necessary at the beginning of the intervention. The risk of harm to the patient is consequently advantageously avoided.

Further features and advantages of the invention will appear in the course of the following description, with reference to the accompaying drawings which illustrate several embodiments by way of a non-limitative example.

DESCRIPTION OF THE PREFERRED EMBODIMENTS

Figure 1:
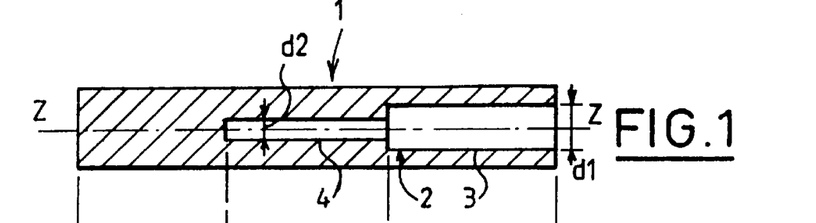
FIG. 1 is a longitudinal sectional view of a first embodiment of a vertebral rod according to the invention.
Figure 2:
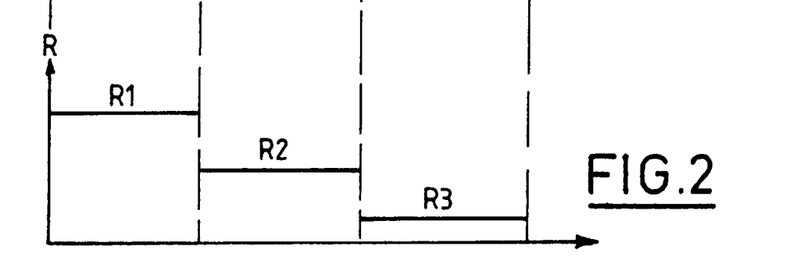
FIG. 2 is a graph representing the variation in the stiffness of the rod of FIG. 1 along its longitudinal axis.

The vertebral rod 1 shown in FIG. 1 has a constant cross section throughout its length and is hollow in a part of its length: indeed, it has a axial bore 2 consisting of a first portion 3 having a diameter d1, and a second portion 4 having a diameter d2 less than d1. In this embodiment, the bore 2 extends along a part of the length of the rod 1, so that the rod has three longitudinal parts of different stiffness: a first part of maximum stiffness R1 corresponding to the solid section of the rod 1, a second part of stiffness R2 less than R1 corresponding to the portion 4 of the bore 2, and lastly a third part of stiffness R3 less than R2 corresponding to the portion 3 of diameter d1, the last portion opening onto the free end of the rod 1.

In the embodiment of FIG. 1, the stiffness varies along the longitudinal axis ZZ of the rod 1 by varying the cross section of the bore 2.

Figure 3:
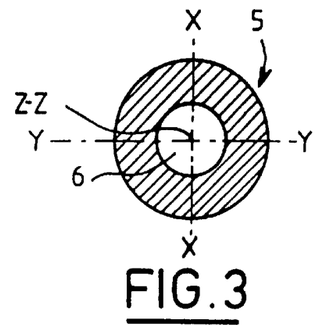
FIGS. 3, 4 and 5 are cross-sectional views of three other embodiments of the rod according to the invention.
Figure 4:
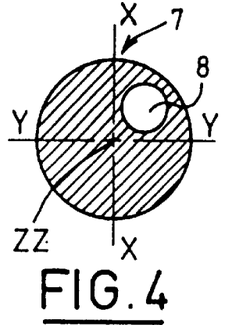
Figure 5:
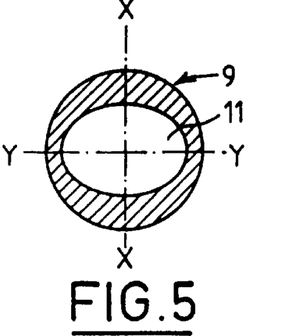

In the embodiments of FIGS. 3, 4 and 5 on the other hand, the stiffness varies in a radial plane about the radial axes XX and YY: the embodiment of FIG. 3 corresponds to a rod 5 having an axial bore 6 of circular section. The rod 7 of FIG. 4 comprises a bore 8 which is also of circular cross section but is radially offset from the longitudinal axis ZZ. Lastly, the rod 9 of FIG. 5 comprises a bore 11 whose surface extends around the longitudinal axis but has a non-circular, for example an oval or elliptic, cross section.

In the various embodiments of FIGS. 3, 4 and 5, the moments of inertia are different about the axes XX and YY, which results in a stiffness which differs according to the axis.

Figure 6:
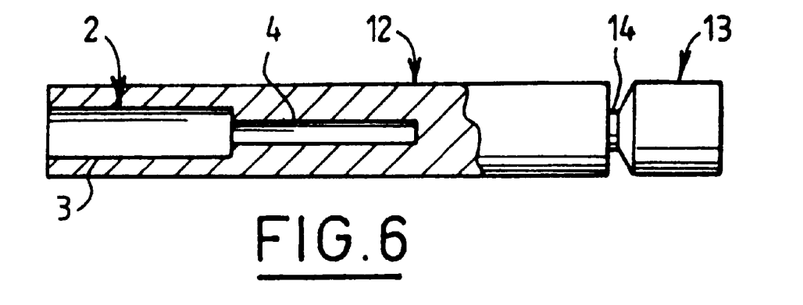
FIG. 6 is a longitudinal sectional view of a fifth embodiment of the rod according to the invention.

The rod 12 of FIG. 6 comprises an axial bore 2 similar to that of rod 1, but is provided at its end remote from the first part 3 of the bore 2, with a separable terminal member 13 having the same cross section as the rest of the rod 12. This terminal member 13 is connected to the rod 12 by a region 14 of reduced strength constituting a fracture initiator.

The terminal member 13 can be removed by bending or torsion with the aid of a suitable tool (not shown) after the rod 12 with the corresponding anchorage means (not shown) have been mounted on the spinal segment.

Owing to the fact that the terminal member 13 may be separated after the mounting of the instrumentation of which the rod 12 is a part, there is obtained after the vertebral correction, a rod whose length is shorter than at the beginning of the intervention, which is an important advantage in cases where the sufficient length of the rod at the end of the intervention is less than the required initial length. This is the case, for example, when restoring a physiological curvature after a surgical operation and ensuring that an end of the rod does not uselessly project, in particular when restoring a lumbar lordosis subsequent to an intervention on a degenerated element, i.e. a painful damaged vertebral disc.

Indeed, initially, the surgeon must in this case use a rectilinear rod of a certain length by means of which he produces a distraction, and then a compression accompanied by a bending of the rod. At the end of this compression and bending, one of the bone anchorage means has slid in the direction of the other and consequently uncovered a free end portion of the rod which becomes a hindrance.

This free end must then be eliminated in one way or another, and this may be easily accomplished without danger to the patient if it is formed by a detachable terminal member such as the terminal member 13 which can be broken off.

Figure 7:
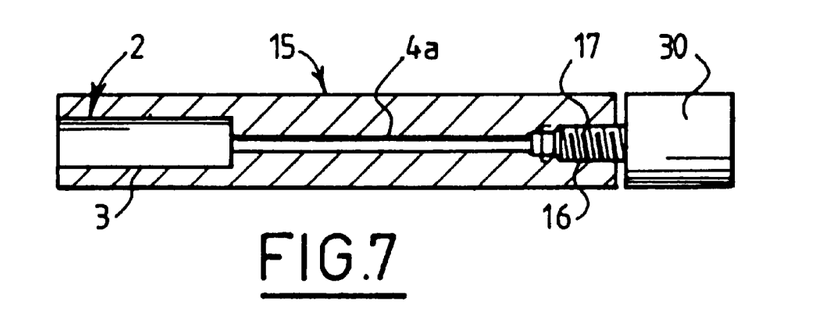
FIG. 7 is a longitudinal sectional view of a sixth embodiment of the rod according to the invention.

In the embodiment of FIG. 7, the rod 15 has an axial bore 2 comparable to that of FIG. 6, but the part 4a of this bore is extended by an axial tapped hole 16 which opens onto the free end of the rod 15. Screwed in the tapped hole 16 is a threaded spigot 17 which axially projects from a terminal member 30 of the same cross section as the rest of the rod 15 with which it forms one piece when the spigot 17 is screwed in the hole 16.

Figure 10:
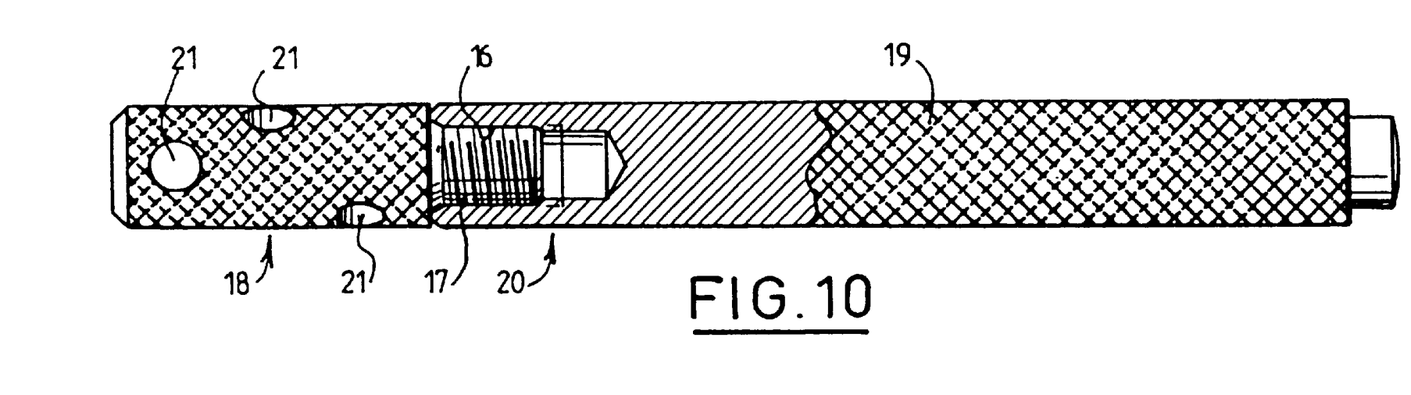
FIG. 10 is a longitudinal view, partly in elevation and partly in section, of a vertebral rod according to a ninth embodiment of the invention.
Figure 15:
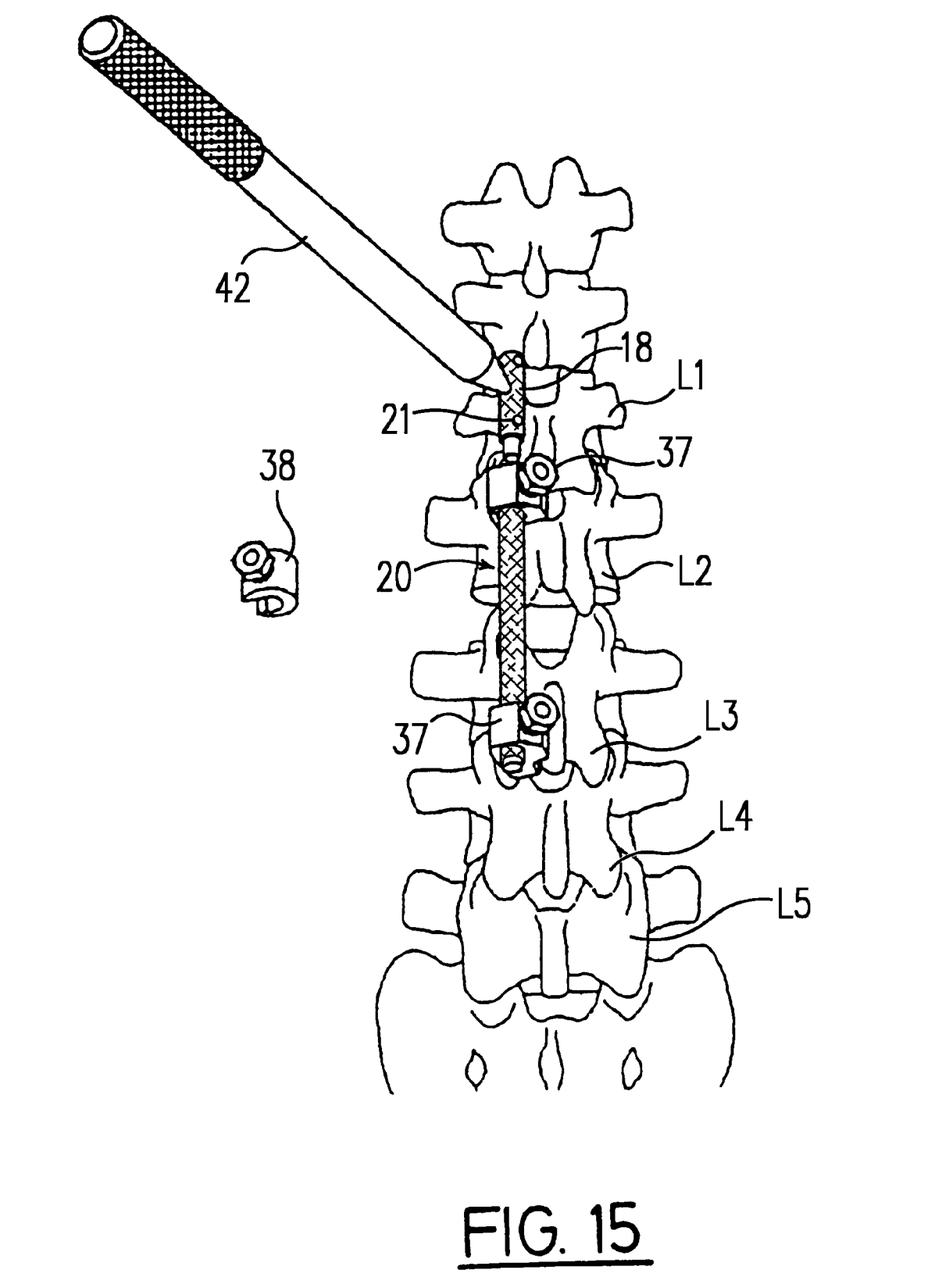

The terminal member 30 may be advantageously identical to the terminal member 18 of FIG. 10 and the rod 15 may have a surface with asperities, such as a knurled surface 19. The terminal member 18 may be unscrewed by hand after the instrumentation has been placed in position by the surgeon, for example by means of a knurling provided on the surface of the terminal member 18, or by means of a suitable unscrewing tool 42 whose end may be inserted in succession in openings 21 provided radially in the terminal member 18 (FIG. 15).

Figure 8:
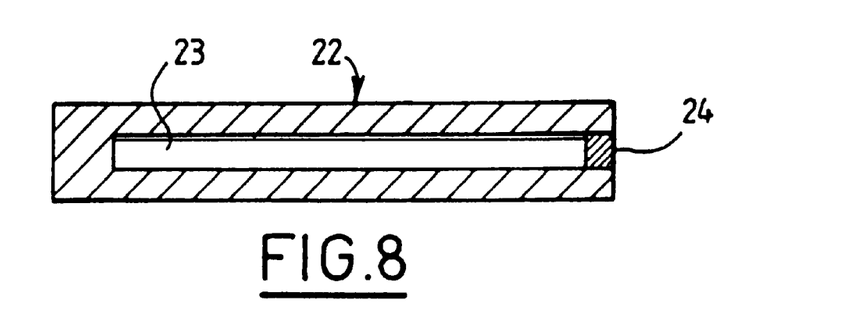
FIG. 8 is a longitudinal sectional view of a seventh embodiment of the rod according to the invention.

In the embodiment of FIG. 8, the rod 22 does not have a separable terminal member but an axial bore 23 of constant cross section extending along the major part of the length of the rod. At one of its ends, the bore 23 terminates in a closing member 24, for example a plug screwed in the end of the bore 23.

Figure 9:
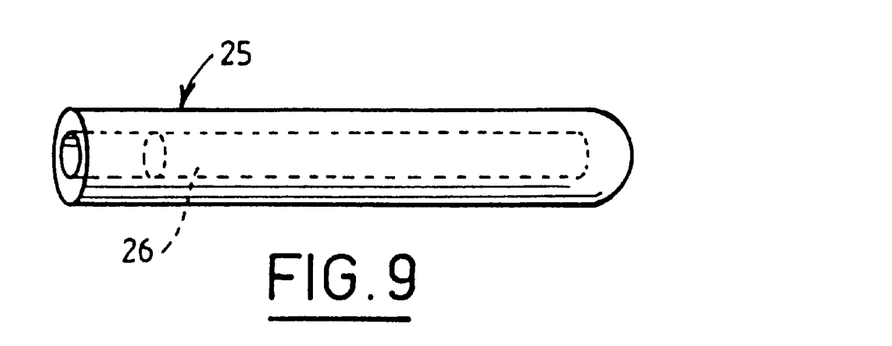
FIG. 9 is a perspective view of an eighth embodiment of the rod according to the invention.

In the embodiment of FIG. 9, the rod 25 comprises an axial bore extending along a part of its length and filled with a core 26, for example composed of a metal, the rest of the rod 25 being composed of a metallic material different from that of the core 26. The latter may also be formed of a plastics material or any other biocompatible materials. In different cases, the core 26 has a stiffness different from that of the material constituting the rest of the rod 25, which permits varying the stiffness along the longitudinal axis.

Figure 11:
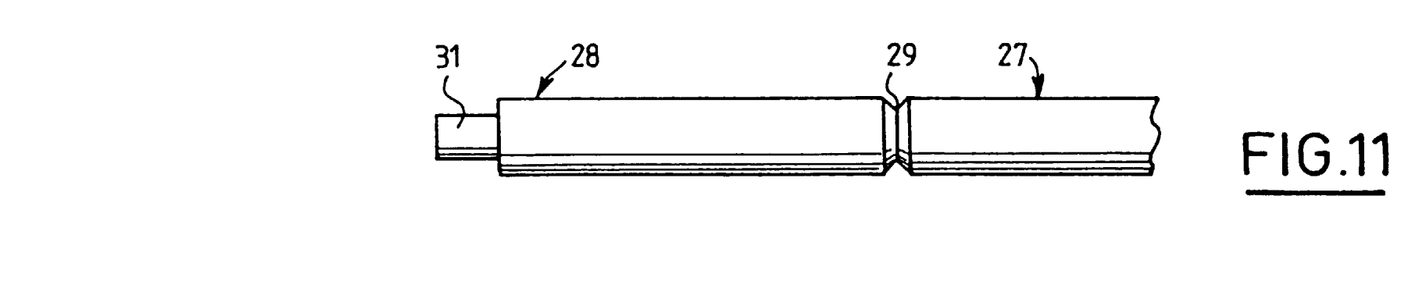
FIG. 11 is a longitudinal elevational view of a vertebral rod according to a tenth embodiment of the invention.

The rod 27 of FIG. 11 does not have an axial bore and is therefore solid throughout its length. This rod 27 is provided at one of its ends with a terminal member 28 which can be broken of f and is connected to the end of the rod 27 by a region 29 of smaller section and consequently of reduced strength, constituting a fracture initiator. The terminal member 28 may be provided with torsion-bending means for breaking it off after the instrumentation including the rod 27 has been placed in position. In the embodiment illustrated in FIG. 11, these torsion means are formed by a shaped end portion 31 which projects from the end of the terminal member 28 remote from the fracture-initiator region 29. This shaped portion is for example of hexagonal cross section and is capable of receiving a corresponding driving tool (not shown). As a variant, the torsion means may be in the form of openings provided radially in the terminal member 28, such as the openings 21 of the terminal member 18 (FIG. 10).

Figure 12:
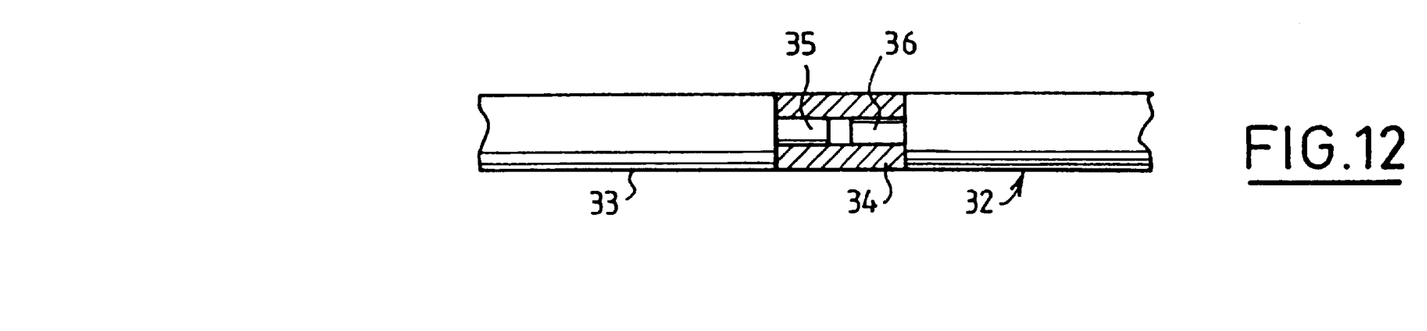
FIG. 12 is a longitudinal elevational view of a rod according to an eleventh embodiment.

In the embodiment illustrated in FIG. 12, the rod 32 is connected to a separable terminal member 33 by a cylindrical intermediate member 34 of the same outside diameter as the rods 32, 33 into which extend terminal spigots 35, 36 of the terminal member 33 and the rod 32 respectively. The member 34 is fixed to the spigots 35, 36 by any suitable means, known per se.

Figure 13:
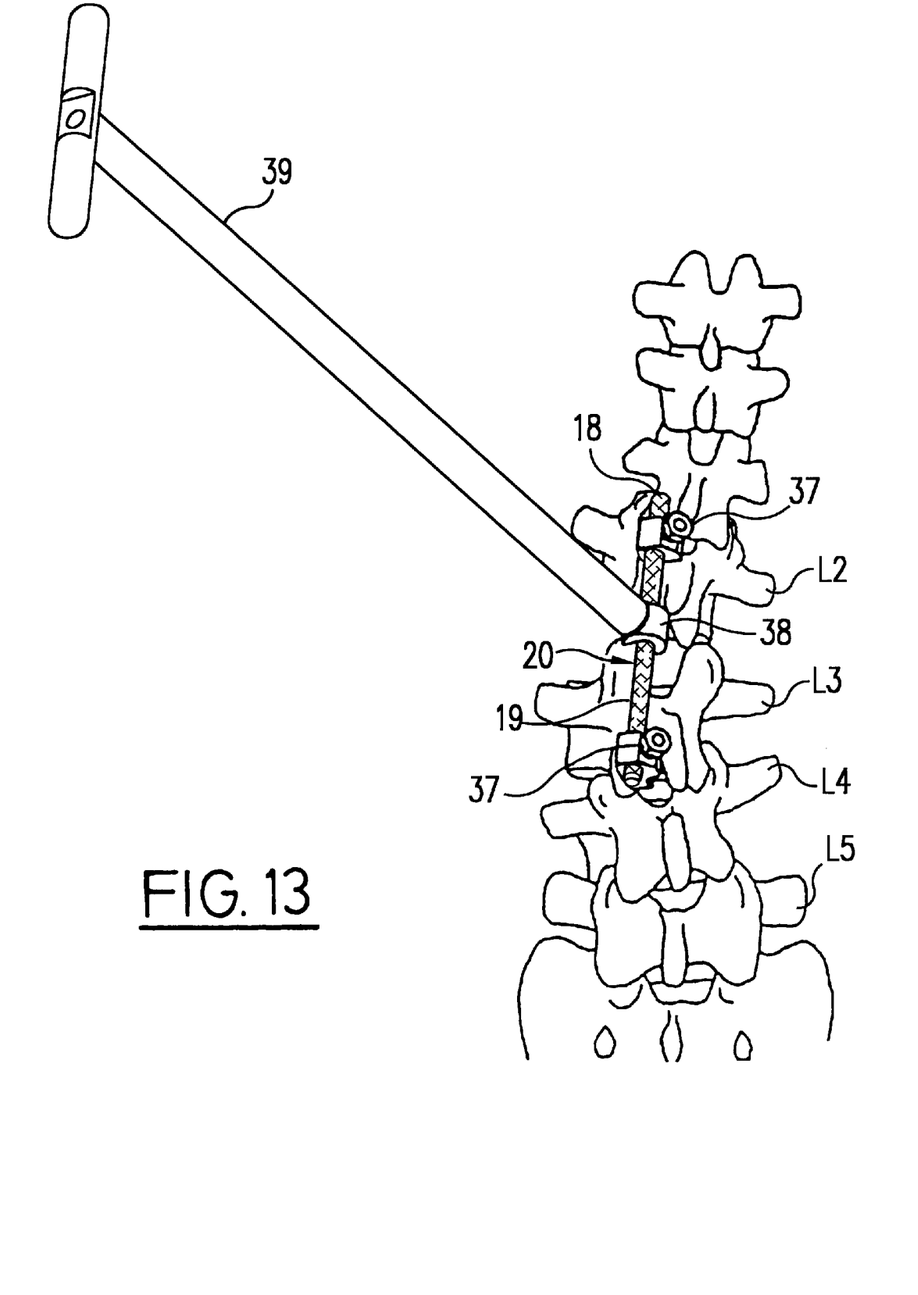
FIGS. 13, 14 and 15 illustrate steps in the placing in position of a rod according to FIG. 9 provided with corresponding bone anchorage implants on a vertebral segment by a surgeon.
Figure 14:
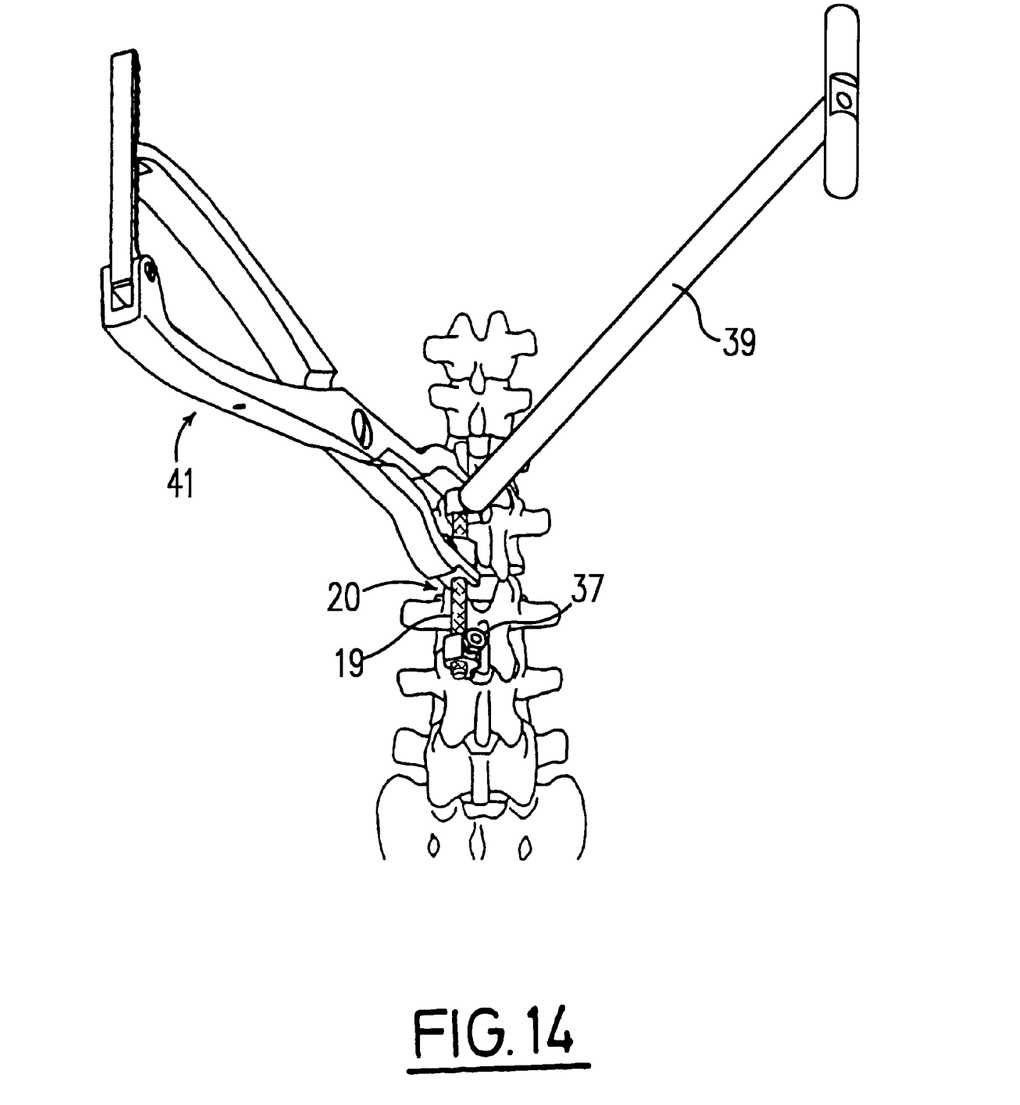

FIGS. 13, 14 and 15 illustrate the steps in the mounting of a vertebral rod 20 provided with a screwed terminal member 18, on two lumbar vertebrae L3, L2 of a spine.

Mounted on the rod 20 are two anchorage implants 37 of known type (bone anchorage screw or hook). The surgeon temporarily places on the rectilinear rod 20, between the anchorage implants 37, a C-shaped collar 38 fixed to the end of the handle 39 of a tool. The lower anchorage implant 37 is fixed in position on the rod 20 and the upper anchorage implant 37 is allowed to slide along the rod.

In FIG. 14, the surgeon uses a pliers 41 for exerting along the axis of the rod 20, by bearing against the collar 38, a force of compression which causes a descent of the upper anchorage implant 37 and moves it toward the lower anchorage implant 37. At the end of this compression, the upper anchorage implant 37 is clamped on the rod 19 in a position short of the terminal member 18. The compression permits restoring for example the alignment of the spinal column.

In the last step (FIG. 15), a tool 42 is used for unscrewing the terminal member 18 and separating it from the rod 20 by inserting the point of the tool 42 in the successive openings 21 provided for this purpose on the terminal member 18. The collar 38 is removed from the rod 20. When the terminal member 18 has been removed, the anchorage means 37 are in position at both ends of the rod without any part of the latter projecting from the anchorage means 37 and without the removal of the terminal member 18 involving any risk for the patient.

The invention is not limited to the various described embodiments and may include many alternative embodiments. For example, the rod 20 may be either solid, as shown in FIG. 10, or provided with an axial bore according to any one of the embodiments of FIGS. 1 to 9. It will be clear that the same is true of the rods 27 and 32.

What is claimed is:

1. A spinal fixation system, comprising:
    a rod including a first longitudinal portion and a second longitudinal portion, said second longitudinal portion defining an end of said rod, said first longitudinal portion has a first outer cross section and said second portion has a second outer cross section generally the same as said first outer cross section, said first longitudinal portion being integrally connected to said second longitudinal portion by a region of said rod having reduced strength relative to said first longitudinal portion and said second longitudinal portion to provide said first longitudinal portion, said second longitudinal portion and said region as a single unitary piece, said region defining a fracture initiator to controllably and selectively separate said second longitudinal portion from said first longitudinal portion by breaking; and
    two bone anchorage implants, said implants each including a fastener to selectively connect to said rod.

2. The system of claim 1 wherein said region h as an area o f r educed outer cross section relative to said first outer cross section and said second outer cross section to define said fracture initiator.

3. The system to claim 1, wherein said first longitudinal portion and said second longitudinal portion each extend along a different part of a longitudinal axis of said elongated rod.

4. The system of claim 1 wherein said second longitudinal portion defines at least one opening configured to receive a driving tool for separation from said first longitudinal portion.

5. The system of claim 1 wherein said end defined by said second longitudinal portion is shaped with a generally hexagonal cross section for engagement by a tool for separating said second longitudinal portion from said first longitudinal portion.

6. A spinal fixation system, comprising:
    a rod including a first longitudinal member and a second longitudinal member extending along a longitudinal axis of said rod, said second longitudinal member defining an end portion of said rod, one of said first longitudinal member and said second longitudinal member defining an opening and another of said first longitudinal member and said second longitudinal member including a spigot, said spigot being engaged in said opening to connect said first longitudinal member and said second longitudinal member and form a substantially uniform outer cross section therebetween generally along the longitudinal axis, said second longitudinal member being detachable from said first longitudinal member by selectively removing said spigot from said opening; and
    two bone anchorage implants, said implants each including a fastener to selectively connect to said rod.

7. The system of claim 6 wherein said opening and said spigot are threaded, and said spigot is threaded into said opening to connect said first longitudinal member and said second longitudinal member together.

8. The system of claim 6 wherein said second longitudinal member defines at least one opening configured to receive a driving tool for rotating said second longitudinal member relative to said first longitudinal member.

9. The system of claim 6 wherein said second longitudinal member defines a knurled outer surface.

10. The system of claim 6 wherein said first longitudinal member defines said opening and said second longitudinal member includes said spigot.

11. A spinal fixation system, comprising:
    a rod including a first longitudinal portion and a second longitudinal portion extending along a longitudinal axis of said rod, said second longitudinal portion defining a detachable end of said rod, said first longitudinal portion defining a first outer cross section along the longitudinal axis and said second longitudinal portion defining a second outer cross section along the longitudinal axis, said first outer cross section being generally the same as said second outer cross section;
    means for connecting said first longitudinal portion to said second longitudinal portion and selectively detaching said second longitudinal portion from said first longitudinal portion, said means defining a maximum outer cross sectional area along the longitudinal axis no greater than a cross sectional area defined by said first outer cross section or said second outer cross section; and
    two bone anchorage implants, each of said implants including a fastener for selective fixation to said rod.

12. The system of claim 11, wherein said means includes an area of reduced strength relative to said first longitudinal portion and said second longitudinal portion to define a fracture initiator to controllably separate said first longitudinal portion from said second longitudinal portion.

13. The system of claim 11, wherein said means includes a threaded opening defined by one of said first longitudinal portion and said second longitudinal portion and a threaded spigot defined by another of said first longitudinal portion and said second longitudinal portion.

14. A method for fixation of a patient's spine, comprising:
    providing a rod, a first bone anchorage implant, and a second bone anchorage implant, the rod including a primary portion and a detachable end portion connected to the primary portion, the rod being provided with a predetermined detachment location therealong, the primary portion and the detachable end portion being selectively separable at the predetermined detachment location, the first and second implants each including a fastener for selective fixation to the rod;
    disposing the rod along the patient's spine, the rod carrying the first implant and the second implant;

fixing the first implant to the primary portion of the rod and to the spine;

moving the second implant along the detachable end portion toward the first implant until the second implant is positioned adjacent the primary portion of the rod;

anchoring the second implant to the spine and the primary portion of the rod; and separating the detachable end portion from the primary portion of the rod at the predetermined detachment location.

15. The method of claim 14 wherein said moving restores alignment of the patient's spine.

16. The method of claim 14 wherein the primary portion of the rod is connected to the detachable end portion by a region of reduced strength, the region of reduced strength constituting a fracture initiator at the predetermined detachment location, and said separating includes breaking off the detachable end portion from the primary portion at the fracture initiator.

17. The method of claim 14 wherein one of the primary portion and the detachable end portion defines an opening and another of the primary portion and the detachable end portion includes a spigot, the spigot selectively engaging the opening to connect the primary portion to the detachable end portion and define the predetermined detachment location along the rod.

18. The method of claim 17, wherein the opening and the spigot are threaded, the spigot being threadedly engageable within the opening to releasably connect the detachable end portion to the primary portion of the rod, and said separating includes unscrewing the spigot from the opening.

19. The method of claim 14 wherein said moving is performed with pliers to provide a force to move the second implant toward the first implant.

* * * * *